United States Patent [19]
Dow, Jr.

[11] Patent Number: 5,120,325
[45] Date of Patent: Jun. 9, 1992

[54] COLOR-MATCHED STERILE ADHESIVE BANDAGES CONTAINING MELANIN-LIKE PIGMENT COMPOSITION

[75] Inventor: James E. Dow, Jr., Hackensack, N.J.

[73] Assignee: Fleshtones Products Co., Inc., Hackensack, N.J.

[21] Appl. No.: 713,827

[22] Filed: Jun. 12, 1991

[51] Int. Cl.⁵ .................. A61F 13/00; A61F 13/02
[52] U.S. Cl. ................................. 604/304; 604/307; 602/41; 602/42; 602/58
[58] Field of Search ............... 604/304, 307; 128/156; 424/447, 448

[56] References Cited

U.S. PATENT DOCUMENTS

| | | | |
|---|---|---|---|
| 3,987,202 | 10/1976 | Okun | 424/70 |
| 4,161,176 | 7/1979 | Harris, II et al. | 128/155 |
| 4,310,509 | 1/1982 | Berglund et al. | 604/307 |
| 4,561,435 | 12/1985 | McKnight et al. | 604/304 |
| 4,699,792 | 10/1987 | Nick et al. | 604/307 |
| 4,710,191 | 12/1987 | Kwiatek et al. | 604/304 |
| 4,728,323 | 3/1988 | Matson | 604/304 |
| 4,745,916 | 5/1988 | Seber | 128/155 |
| 4,895,727 | 1/1990 | Allen | 424/642 |
| 4,990,144 | 2/1991 | Blott | 604/304 |

Primary Examiner—David Isabella
Assistant Examiner—Dinh X. Nguyen
Attorney, Agent, or Firm—Carl W. Battle

[57] ABSTRACT

A sterile bandage suitable for external application to a wound or injury of the human skin comprising a backing layer, a non-toxic pigmented composition coated onto or embedded into the top side of said backing layer, wherein said pigmented composition comprises one or more pigments having a melanin likeness in appearance so as to substantially match the appearance of said human skin.

16 Claims, No Drawings

COLOR-MATCHED STERILE ADHESIVE BANDAGES CONTAINING MELANIN-LIKE PIGMENT COMPOSITION

BACKGROUND OF THE INVENTION

Adhesive bandages are well known and have been used as wound coverings to aid in the healing process. Commercial adhesive bandages have been marketed by Johnson & Johnson Consumer Products, Inc. of New Brunswick, N.J.; Colgate-Falmolive Company of New York, N.Y.; and several other manufacturers. These bandages may come in a variety of shapes and sizes, but are generally of a pinkish and non-melarin-like color. The bandages of the prior art do not provide any significant cosmetic benefits when applied to human skin containing relatively high concentrations of melanin.

The present invention provides significant cosmetic benefits when applied to human skin containing relatively high levels of melanin. The bandages of this invention contain a pigmented composition comprising melanin pigments or pigments having a melanin-like color and appearance. This pigmented composition makes the bandages of this invention substantially indistinguishable in appearance from human skin containing relatively high levels of melanin.

SUMMARY OF THE INVENTION

This invention relates to an article of manufacture comprising a sterile bandage suitable for external application to a wound or injury of the human skin comprising a backing layer and a non-toxic pigmented composition coated onto or embedded into said backing layer wherein said pigmented composition comprises one or more pigments having a melanin likeness in appearance so as to substantially match the appearance of said human skin. Preferably the bandage comprises:

a) a backing layer having a bottom side and a top side;
b) an adhesive layer applied to said bottom side of said backing layer;
c) an absorbent pad attached to a portion of said bottom side of said backing layer by a portion of said adhesive layer; and
d) a non-toxic pigmented composition coated onto or embedded into said top side of said backing layer wherein said pigmented composition comprised one or more pigments having a melanin likeness in appearance so as to substantially match the appearance of said human skin.

The adhesive bandages of the invention are useful in aiding the healing of external wounds while also providing some cosmetic benefits in concealing the wounds by being color-matched to the appearance of melanin-containing human skin. The pigment compositions used in this invention can be melanin or any natural or synthetic pigments or colorants, or combinations thereof, which have a melanin likeness in color and appearance. The preferred pigmented compositions contain a brownish-black pigment or a reddish-brown pigment or combinations thereof. The bandages preferably contain a medicament or an antimicrobial agent.

DETAILED DESCRIPTION

The present invention relates to an article of manufacture in the form of bandage which has both substantial medicinal and cosmetic benefits. The present invention specifically relates to an article of manufacture comprising a sterile bandage suitable for external application to a wound or injury of the human skin comprising a backing layer and a non toxic pigmented composition coated onto or embedded into said backing layer wherein said pigmented composition comprises one or more pigments having a melanin likeness in appearance so as to substantially match the appearance of said human skin. Preferably the invention is a sterile adhesive bandage suitable for external application to a wound of the human skin comprising:

a) a backing layer having a bottom side and a top side;
b) an adhesive layer applied to said bottom side of said backing layer;
c) an absorbent pad attached to a portion of said bottom side of said backing layer by a portion of said adhesive layer; and
d) a non-toxic pigmented composition coated onto or embedded into said top side of said backing layer wherein said pigmented composition comprises one or more pigments having a melanin likeness in appearance so as to substantially match the appearance of said human skin.

The bandages of this invention are useful for their aid in healing external wounds and injuries and for their substantial cosmetic benefit, especially when applied to human skin containing a relatively high level of melanin. The bandages can be in the form of wraps or adhesive bandages.

The backing layer of this invention can be any inert, flexible material, such as polyethylene, polyester, polypropylene, polyvinyl chloride, polystyrene, polyethylene terephthalate, rayon, nylon, acetate, silk, cotton, wool, or any other natural or synthetic polymer or fiber or any combinations thereof. The backing layer may contain one or more metal layers and/or one or more layers of any natural or synthetic films or fibers. The preferred backing layer for this invention comprises a flexible woven fabric, such as nylon, or a polyvinyl chloride film. The backing layer of this invention has a top side and a bottom side. Preferably the top side of the backing layer has a multiplicity of folds and grooves in the surface thereof so as to simulate the texture of human skin. Also, preferably the backing layer is perforated to make it porous and breathable.

An adhesive layer can be applied to the bottom side of said backing layer. This adhesive layer functions to attach the bandage firmly to the skin. Any adhesive composition can be used as the adhesive layer provided that it is a pressure-sensitive adhesive which firmly attaches the bandage to the skin, is resistant to moisture and is removable without damage to the skin or wound. Preferably the adhesive layer is an acrylic adhesive prepared from polymer and copolymers of acrylic esters and copolymers of acrylic esters and other ethylenically-unsaturated monomers. Preferably the acrylic adhesive is selected from the group consisting of butyl acrylate, ethyl acrylate, ethyl hexyl acrylate, vinyl acetate/ethylene acrylate and mixtures thereof. The acrylic adhesive of this invention can be prepared by conventional processes which are well known in the art, including suspension, dispersion, emulsion or solution polymerization techniques.

In the preferred embodiment of this invention a peelable protective layer is applied over the adhesive layer and is removed at the time of use to expose the adhesive layer. The protective layer can be comprised of any substantially non-stick paper, polymer, fabric or other material.

The adhesive bandages of this invention comprise an absorbent pad attached to a portion of the bottom side of the backing layer. The absorbent pad is preferably attached to said backing layer by a portion of said adhesive layer. The absorbent pad is preferably attached in the center of the bandage and may be comprised of cotton, wool, polymeric foam or any other natural or synthetic absorbent material. The absorbent paid is preferably enclosed within a porous or perforated non stick polymer such as teflon, linear polyethylene or the like.

It is critical to this invention that a non-toxic, pigmented composition is coated onto or embedded into the top side of the backing layer, wherein said pigmented composition comprises one or more pigments having a melanin likeness in appearance so as to substantially match the appearance of human skin. Any non-toxic coating or dyeing composition can be used in this invention provided that the composition comprises a melanin or melanin-like pigment or colorant. The preferred pigment for use in this invention is melanin. Melanin is a brownish black or reddish-brown pigment that occurs naturally in the retina, skin, and hair of higher animals. Preferred melanin pigments are eumelanin, spiomelanin, phaeomelanin and mixtures thereof.

The melanin pigments can be extracted from natural sources such as skin, hair, features, fur, insect cuticles and other natural sources. The melanin pigments can also be synthesized, such as (1) by the oxidative polymerization of 5,6-dihydroxyindoles derived enzymatically (i.e. via tyrosinase) from tyrosine via dihydroxyphenylalanine, or (2) by oxidative polymerization of cysteinyl-dihydroxyphenylalanines via 1, 4-benzothiazine intermediates.

The amount of melanin pigment used in the pigmented compositions of this invention can vary and can be adjusted to correspond to the color of the skin of the subjects by whom the bandages will be used. Preferably the pigmented composition comprises from about 1% to about 50% by solid weight of the melanin pigment. Other conventional ingredients can also be added to the pigmented composition, such as fillers, solvents, pacifiers, stabilizers, surfactants, adhesion promoters, extenders, leveling agents and the like.

The pigmented compositions of this invention can also contain melanin-like pigment(s) in addition to or in lieu of the melanin pigments. Melanin-like pigment(s) means one or more pigments which have the substantial appearance and color of melanin. Suitable pigments include any of the organic or inorganic pigments which when used alone or in combination would have a melanin-like appearance and color. These inorganic pigments can be metallic oxides (such as iron, titanium, zinc, cobalt or chromium or mixtures thereof); metal powder suspension (such as gold or aluminum); lead chromates; carbon blacks; and earth colors (such as siennas, ochers and umbers). The pigments can also be organic pigments such as rhodopsin, chlorophyll, xanthophyll, indigo, flavone, carotene and other animal or vegetable pigments, and synthetic pigments such as phthalocyanines, lithols, to toluidines, metal dyes, azo dyes and the like. The pigment or mixtures thereof are preferably selected such that they have a brownish-black or reddish-brown appearance or combinations thereof. These pigments are preferably used at concentrations of about 0.5% to about 98% by solid weight of the pigmented composition.

A preferred pigmented composition having a melanin-like appearance comprises by solid weight about 20-40% of a red pigment, about 2-10% of a blue pigment, about 35-55% of a yellow pigment and about 5-25% of a black pigment.

Another preferred pigmented composition having a melanin-like appearance comprises by solid weight about 1-15% of a yellow pigment, about 1-10% of a red pigment, about 0.5-10% of a black pigment and about 70-97.5% of a white pigment.

Another preferred pigmented composition having a melanin-like appearance comprises by solid weight about 35-45% of a yellow pigment, about 25-35% of a red pigment and about 25-35% of a black pigment.

The pigmented compositions containing the melanin-like pigments can also contain a variety of conventional ingredients as described earlier. The pigmented compositions of this invention are non toxic and preferably are water insoluble and non-leachable, especially after drying and curing. The pigmented compositions preferably comprise by solid weight less than 5 parts per million of each of the metals selected from the group consisting of antimony, barium, cadmium, chromium, cobalt, lead and nickel, less than 0.35 parts per million selenium, less than 2 parts per million arsenic and less than 2 parts per million mercury.

The pigmented coating can be applied to the backing layer by any conventional method known in the art, such as dipping, spraying, brushing, rolling and the like.

The bandages of this invention preferably contain one or more medicaments absorbed, coated or otherwise contained therein. Suitable medicaments include, for example, anti-inflammatory agents such as aminoarylcarboxylic acid derivatives arylacetic acid derivatives, arylbutyric acid derivatives, arylcarboxylic acids, arylpropionic acid derivatives, pyrazoles, pyrazolones, salicylic acid derivatives, thiazinecarboxamides and other nonsteroidal anti-inflammatory agents such as glucocorticoid and the like. Suitable medicaments also include antiseptic and disinfectant agents such as, alcohols (such as dichlorobenzyl alcohol, ethyl alcohol and isopropyl alcohol); aldehydes (such as formaldehyde solution, and glutaraldehyde); dyes (such as acriflavine, amiinacrine, brilliant green, ethacridine, gentian violet, magenta I, methyl blue and phenacridane chloride); guanidines (such as alexidine, ambazone, chlorhexidine, and picloxydine); halogens/halogen compounds (such as bismuth iodide oxide, bismuth iodosubgallate, bismuth tribromophenate, bornyl chloride, calcium iodate, chlorinated lime, cloflucarban, fluorosalan, iodic acid, iodine, iodine monochloride, iodine trichloride, iodoform, methenamine tetraiodine, oxychlorosene, povidone-iodine, sodium hypochlorite, sodium iodate, symclosene, thymol iodide, triclocarban, triclosan, and troclosene potassium); mercurial compounds (such as hydrargaphen, meralein sodium, merbromin, mercuric chloride, mercuric chloride ammoniated, mercuric sodium p-phenolsulfonate, mercuric succinimide, mercuric sulfide red, mercurophen, mercurous acetate, mercurous chloride, mercurous iodide, nitromersol, potassium tetraiodomercurate (II), potassium triiodomercurate (II) solution, thimerfonate sodium and thimerosal); nitrofurans (such as furazolidone, 2-(methoxymethyl)-5-nitrofuran, nidroxyzone, nifuroxime, nifurzide and nitrofurazone); peroxides/permanganates (such as calcium peroxide, hydrogen peroxide, hydrogen peroxide solution 3%, magnesium peroxide, potassium permanganate, strontium peroxide, succinyl peroxide, urea hydrogen peroxide, and zinc permanganate); phenols (such as acetomeroctol, bithionol cadmium salicylate, carvacrol, chloroxylenol, clorophene, cresote, cresol(s), p-Cresol, fenticlor, hexachlorophene, 1-naphthyl salicylate, 2-naphthyl salicylate, 2,4,6 tribromo-m-cresol, and 3',4',5-trichlorosalicylanilide); quaternary ammonium compounds (such as amantanium bromide, benzethonium chloride, benzoxonium chloride, bisdequalinium chloride, cetalkonium chloride, cethexonium bromide, cetylpyridinium chloride, dequalinium acetate, dequalinium chloride, dodecarbonium chloride, domiphen bromide, halimide ®, laurolinium acetate, methylbenzethonium chloride, phenoctide, tibezonlum iodide, and triclobisonium chloride; quinolines (such as aminoquinuride, benzoxiquine, broxyquinoline, chloroxine, chlorquinaldol, cloxyquin, ethylhydrocupreine, euprocin, halquinol, hydrastine, 8-hydroxyquinoline, 8-hydroxyquinoline sulfate, and iodochlorhydroxyquin); silver compounds (such as silver bromide, silver fluoride, silver lactate, silver nitrate, and silver protein); others (such as aluminum acetate solution, aluminum subacetate solution, aluminum sulfate, 3-amino-4-hydroxybutyric acid, boric acid, chlorhexidine, chloroazodin, m-Cresyl acetate, cupric sulfate, dibromopropamidine, echthammol, Negatol ®,noxytiolin, ornidazole, beta-propiolactone and alpha-terpineol).

Suitable medicaments also include anesthetic agents such as ambucaine, benzocaine dimethocaine, dyclonine, ethyl chloride, lidocaine, mepivacaine, methyl chloride, phenol, pramoxine, salicyl alcohol and the like. Also included are antiarrhythmic agents, narcotic analgesic agents and non-narcotic analgesic agents and the like.

In another preferred embodiment the bandages of this invention have chemically bound to the surfaces thereof one or more antimicrobial agents selected from the group consisting of quaternary ammonium compounds, organosilicone quaternary ammonium compounds, cetyl pyridinium compounds, guanidine compounds, bis-guanidine compounds, and isothiouronium halide compounds. These antimicrobial agents are substantially non leachable from the surface of the bandages and are substantially permanently attached thereto. Thus, the bandages would have permanent antibacterial and/or antimicrobial activity which would make the bandages self-disinfecting. The antimicrobial agents can be permanently attached to the surfaces of the bandages by any suitable means such as chemical linking using multifunctional reactive organics (such as bis carbenes or bis nitrenes), silane coupling systems, plasma activation, flame activation, chemical treatment and other polymer grafting techniques. They can also be incorporated into the adhesive composition and the pigmented composition and applied to the surfaces of the bandages.

The preferred antimicrobial agents are selected from the group consisting of n-octadecyldimethyl[3-(trimethoxysilyl)propyl] ammonium chloride, n-tetradecyl dimethyl [3-(trimethoxysilyl) proply] ammonium chloride, n-decyldimethyl[3-(trimethoxysilyl)propyl] ammonium chloride, n-didodecylmethyl[3-(trimethoxysilyl)propyl] ammonium chloride, n-dodecyldimethyl [3-(trimethoxysilyl) propyl] ammonium chloride, 2-(3 trimethoxysilylpropyl)-N-cetyl pyridinium bromide and (trimethoxysilyl propyl) isothiouronium.

The following examples are prevented to further demonstrate this invention. The examples are intended in an illustrative and not a limitative sense. The invention includes all the embodiments described herein and all equivalents thereof.

EXAMPLE I

A pigmented composition within the scope of this invention was prepared by mixing into a standard ink formulation pigments comprising 30% by weight red pigment, 5% by weight blue pigment, 45% by weight yellow pigment, and 20% by weight black pigment in accordance with Pantone Matching System Color Formula No. 469, available from Pantone, Inc., 55 Nickerbocker Road, Moonachie, N.J. 07074. The pigmented composition was applied to the top side of polyvinyl chloride film and cured. This film was then made into sterile adhesive bandages. The finished bandages had a melanin appearance and color.

EXAMPLE II

Following the procedures of Ex. I a pigmented composition was prepared using pigments comprising by weight 35.3% red pigment, 5.9% blue pigment, 52.9% yellow pigment and 5.9% black pigment in accordance with Pantone Matching System Color Formula No 470. The final product was made in a similar way as in Example I, in creating a sterile adhesive bandage as claimed. The finished bandages had a melanin appearance and color.

EXAMPLE III

Following the procedures of Example I, a pigmented composition was prepared using pigments comprising by weight 4% red pigment, 5.1% yellow pigment, 3.4% black pigment and 87.5% white pigment in accordance with Pantone Matching System Color Formula No. 4655. The final product was made in a similar way as in Example I, in creating a sterile adhesive bandage as claimed. The finished bandages had a melanin appearance and color.

EXAMPLE IV

In a similar way as prepared in Example I a pigmented composition was prepared using pigments comprising by weight 1.3% yellow pigment, 1% red pigment, 0.8% black pigment and 96.9% white pigment in accordance with Pantone Matching System Color Formula No. 4675. The final product was made in a similar way as in Example I, in creating a sterile adhesive bandage as claimed. The finished bandages had a melanin appearance and color.

EXAMPLE V

In a similar way as prepared in Example I a pigmented composition was prepared using pigments comprising by weight 10.2% yellow pigment, 8% red pigment, 6.8% black pigment and 75% white pigment in accordance with Pantone Matching System Color Formula No. 4645. The final product was made in a similar way as in example I, in creating a sterile adhesive bandage as claimed. The finished bandages had a melanin appearance and color.

EXAMPLE VI

In a similar way as prepared in Example I a pigmented composition was prepared using pigments comprising by weight 40.9% yellow pigment, 31.8% red pigment, and 27.3% black pigment in accordance with Pantone Matching System Color Formula No. 4625. The final product was made in a similar way as in Example I, in creating a sterile adhesive bandage as claimed. The finished bandages had a melanin appearance and color.

I claim:

1. An article of manufacture comprising a sterile bandage suitable for external application to a wound or injury of the human skin comprising a backing layer and a non-toxic pigmented composition coated onto or embedded into said backing layer substantially matching the appearance of human skin, wherein said pigmented composition comprises from about 0.5% to about 98% by solid weight of at least one melanin pigment or pigment having substantially the color and appearance of melanin, said melanin pigment being selected from the group consisting of melanin, eumelanin, spiomelanin, phaeomelanin and mixtures thereof.

2. An article of manufacture comprising a sterile adhesive bandage suitable for external application to a wound or injury of the human skin comprising:
   (a) a backing layer having a bottom side and a top side;
   (b) an adhesive layer applied to said bottom side of said backing layer;
   (c) an absorbent pad attached to a portion of said bottom side of said backing layer by a portion of said adhesive layer; and
   (d) a non-toxic pigmented composition coated onto or embedded into said top side of said backing layer substantially matching the appearance of human skin, wherein said pigmented composition comprises from about 0.5% to about 98% by solid weight of at least one melanin pigment or pigment having substantially the color and appearance of melanin, said melanin pigment being selected from the group consisting of melanin, eumelanin, spiomelanin, phaeomelanin and mixtures thereof.

3. The article of claim 2 wherein said pigment is a brownish-black pigment.

4. The article of claim 2 wherein said pigment is a reddish-brown pigment.

5. The article of claim 2 wherein said pigmented composition comprises by solid weight about 20–40% of a red pigment, about 2–10% of a blue pigment, about 35–55% of a yellow pigment and about 5–25% of a black pigment.

6. The article of claim 2 wherein said pigmented composition comprises by solid weight about 1–15% of a yellow pigment, about 1–10% of a red pigment, about 0.5–10% of a black pigment and about 70–97.5% of a white pigment.

7. The article of claim 2 wherein said pigmented composition comprises by solid weight about 35–45% of a yellow pigment, about 25–35% of a red pigment and about 25–35% of a black pigment.

8. The article of claim 2 wherein said pigmented composition comprises by solid weight less than 5 parts per million of each of the metals selected from the group consisting of antimony, barium, cadmium, chromiun, cobalt, lead and nickel, less than 0.35 parts per million selenium, less than 2 parts per million arsenic and less than 2 parts per million mercury.

9. The article of claim 2 wherein said pigmented composition is water insoluble.

10. The article of claim 2 wherein said backing layer is comprised of a polymeric film.

11. The article of claim 2 wherein said backing layer is comprised of a flexible, woven fabric.

12. The article of claim 2 wherein said bandage contains a medicament.

13. The article of claim 2 wherein said bandage has chemically bonded to the surfaces thereof one or more substantially non-leachable antimicrobial agents selected from the group consisting of quaternary ammonium compounds, organosilicone quaternary ammonium compounds, cetyl pyridinium compounds, guanidine compounds, bis-quanidine compounds, and isothiouronium halide compounds.

14. The article of claim 13 wherein said antimicrobial agent is selected from the group consisting of n-octadecyldimethyl[3 (trimethoxysilyl)propyl] ammonium chloride, n-tetradecyldimethyl 3-(trimethoxysilyl) propyl] ammonium chloride, n decyldimethyl[3-(trimethoxysilyl)propyl] ammonium chloride, n-didodecylmethyl[3-(trimethoxysilyl)propyl] ammonium chloride, n dodecyldimethyl[3-(trimethoxysilyl)propyl] ammonium chloride, 2-(3-trimethoxysilylpropyl)-N-cetyl pyridinium bromide and (trimethoxysilyl propyl) isothiouronium.

15. The article of claim 2 wherein said adhesive layer is comprised of polymeric acrylic adhesive.

16. The article of claim 15 wherein said acrylic adhesive is selected form the group consisting of nutyl acrylate, ethyl acrylate, ethyl hexyl acrylate, vinyl acetate/ethylene acrylate and mixtures thereof.

* * * * *